(12) United States Patent
Eskuri

(10) Patent No.: US 7,993,285 B2
(45) Date of Patent: Aug. 9, 2011

(54) MEDICAL DEVICE HAVING FLEXIBLE DISTAL TIP

(75) Inventor: Alan D. Eskuri, Hanover, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1464 days.

(21) Appl. No.: 10/288,173

(22) Filed: Nov. 5, 2002

(65) Prior Publication Data
US 2004/0087876 A1 May 6, 2004

(51) Int. Cl.
*A61B 5/00* (2006.01)
(52) U.S. Cl. .......................... 600/585; 600/139
(58) Field of Classification Search .............. 600/585, 600/433, 435, 523, 528, 139
See application file for complete search history.

(56) References Cited

U.S. PATENT DOCUMENTS

| | | | |
|---|---|---|---|
| 3,674,014 A | 7/1972 | Tillander | |
| 3,749,086 A | 7/1973 | Kline et al. | |
| 3,794,041 A * | 2/1974 | Frei et al. | 606/108 |
| 4,545,081 A * | 10/1985 | Nestor et al. | 623/14.13 |
| 5,042,475 A * | 8/1991 | LaBombard | 128/207.14 |
| 5,222,487 A * | 6/1993 | Carr et al. | 128/200.26 |
| 5,402,799 A * | 4/1995 | Colon et al. | 600/585 |
| 5,549,580 A | 8/1996 | Diaz | |
| 5,596,996 A | 1/1997 | Johanson et al. | |
| 5,769,796 A * | 6/1998 | Palermo et al. | 600/585 |
| 5,772,609 A | 6/1998 | Nguyen et al. | |
| 5,827,225 A | 10/1998 | Ma Schwab | |
| 5,902,254 A * | 5/1999 | Magram | 600/585 |
| 5,993,415 A | 11/1999 | O'Neil et al. | |
| 6,074,412 A * | 6/2000 | Mikus et al. | 607/105 |
| 6,099,457 A * | 8/2000 | Good | 600/8 |
| 6,139,510 A * | 10/2000 | Palermo | 600/585 |
| 6,183,420 B1 * | 2/2001 | Douk et al. | 600/462 |
| 6,308,091 B1 * | 10/2001 | Avitall | 600/374 |
| 6,430,426 B2 * | 8/2002 | Avitall | 600/374 |
| 6,505,629 B1 * | 1/2003 | Mikus et al. | 128/898 |
| 6,616,617 B1 * | 9/2003 | Ferrera et al. | 600/585 |
| 6,638,266 B2 * | 10/2003 | Wilson et al. | 604/523 |
| 2002/0143348 A1 * | 10/2002 | Wallace et al. | 606/157 |
| 2003/0032859 A1 * | 2/2003 | Belson | 600/114 |

FOREIGN PATENT DOCUMENTS

JP 03168156 7/1991

OTHER PUBLICATIONS

U.S. Appl. No. 09/972,276, filed Oct. 5, 2001, Skujins et al.

* cited by examiner

*Primary Examiner* — Sanjay Cattungal
(74) *Attorney, Agent, or Firm* — Seager, Tufte & Wickhem, LLC

(57) ABSTRACT

A medical device having a flexible distal tip. In some embodiments, a medical device includes a shaft and a distal tip. The distal tip can include an outer member having one or more balls disposed therein.

16 Claims, 3 Drawing Sheets

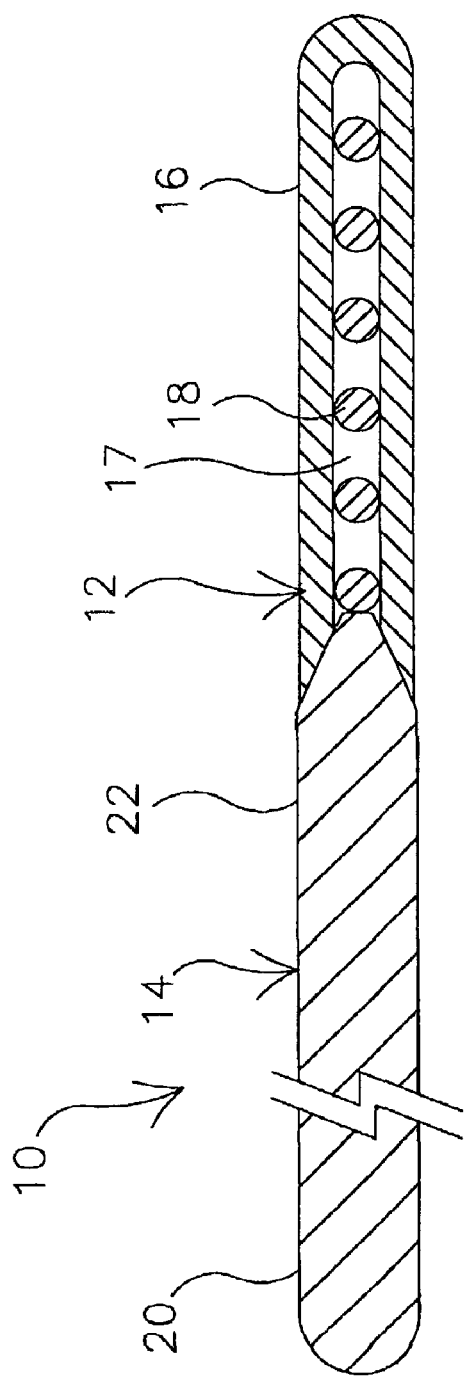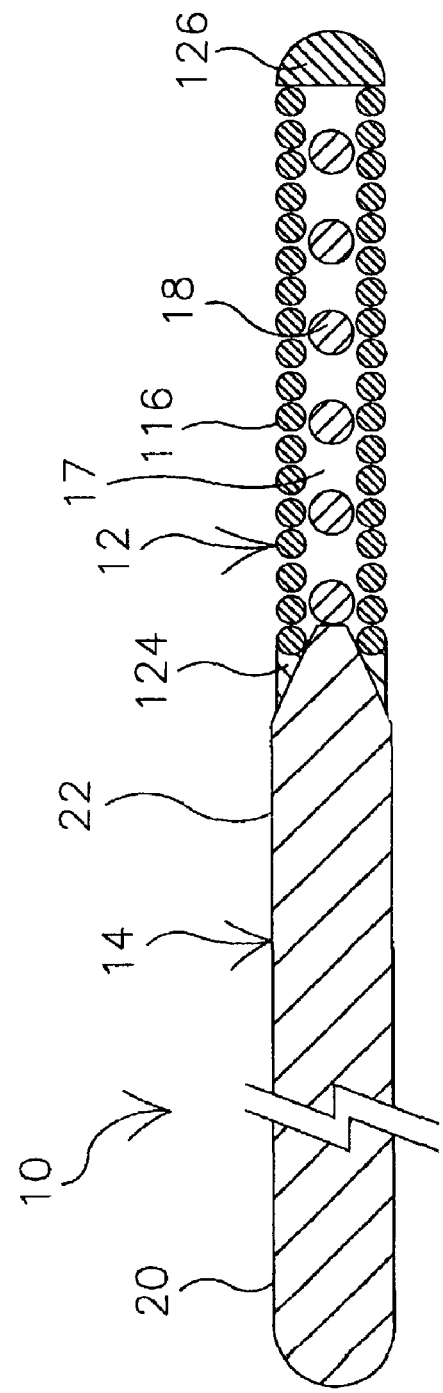

MEDICAL DEVICE HAVING FLEXIBLE DISTAL TIP

FIELD OF THE INVENTION

The invention generally pertains to medical devices. More particularly the invention relates to medical devices having a flexible distal tip.

BACKGROUND

The use of medical devices, for example, the use of intravascular catheters and guidewires, has become an effective method for treating many types of disease. In general, an intravascular device is inserted into the vascular system of the patient and navigated through the vasculature to a desired target site. Using this method, virtually any target site in the patient's vascular system may be accessed, including the coronary, cerebral, and peripheral vasculature.

Frequently the path taken by an intravascular device through the vascular system is tortuous, requiring the device to change direction frequently. In some cases, it may even be necessary for the catheter to bend ninety degrees or more. In order for the device to conform to a patient's tortuous vascular system, it may be desirable that the intravascular device be very flexible, particularly near the distal end.

SUMMARY

The invention provides several alternative designs, materials, and manufacturing methods for medical devices. Some example embodiments include a medical device (e.g., a catheter, guidewire, etc.) having an elongated proximal shaft portion and a flexible distal tip. The distal tip can include an outer member having one or more balls, beads, or other like members disposed therein. In some embodiments, the outer member can comprise a outer sheath or a coil.

BRIEF DESCRIPTION OF THE DRAWINGS

FIG. 5 is a cross-sectional view of a fourth alternative medical device, wherein the balls are loosely packed within the outer member; and FIG. 6 is a cross-sectional view of a fifth alternative medical device, wherein the balls are loosely packed within the coil.

DETAILED DESCRIPTION

Figure 1:
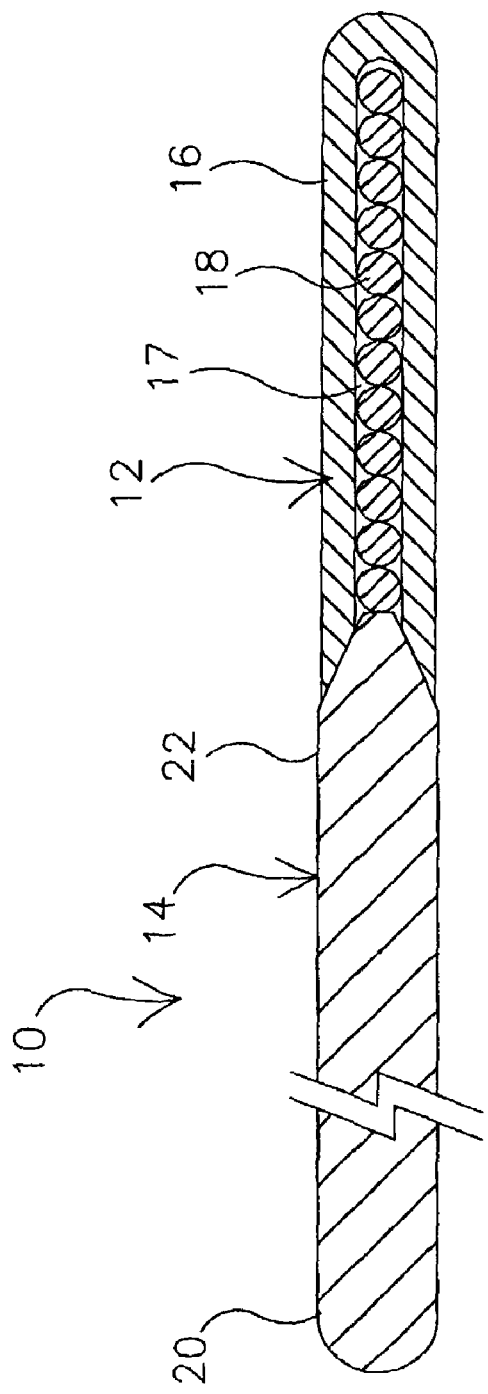
FIG. 1 is cross-sectional view of a medical device having a flexible distal tip that includes an outer member having one or more balls disposed therein.

The following description should be read with reference to the drawings wherein like reference numerals indicate like elements throughout the several views. The detailed description and drawings illustrate example embodiments of the claimed invention.

It can be difficult for medical devices such as catheters or guidewires to navigate the anatomy, for example the tortuous network of blood vessels within a living being. Catheters, guidewires, etc. are, thus, designed to have a degree of flexibility, particularly near the distal end. In addition, medical devices also may need a level of pushability and torquability to allow a user to apply force in the distal direction as well as apply rotational force. In order to incorporate these characteristics, a medical device often has a relatively stiff proximal portion and a relatively flexible distal portion.

The invention relates to a medical device having a flexible distal tip. In the embodiments shown in FIGS. 1-6, the medical device is depicted as a guidewire. However, the device is not intended to be limited to guidewires. It can be appreciated that the medical device could be any intravascular device or be any device designed to pass through an opening or body lumen. For example, the device may comprise a catheter (e.g., therapeutic, diagnostic, or guide catheter), endoscopic device, laproscopic device, or any other medical device.

Refer now to FIG. 1, which is a partial cross-sectional view of a medical device 10 that is a guidewire. The guidewire 10 includes an elongate shaft 14 having a distal tip 12. Distal tip 12 can be attached to, be integral with, or be a portion of shaft 14. In some embodiments, distal tip 12 includes an outer member 16 having one or more balls 18 disposed therein. Distal tip 12 is designed to provide distal flexibility to device 10 and/or shaft 14.

Shaft 14 has a proximal portion 20 and a distal portion 22. Shaft 14 can be made of any suitable material including, for example, metals, metal alloys, polymers, or the like, or combinations or mixtures thereof. Some examples of suitable metals and metal alloys include stainless steel, such as 304v stainless steel; nickel-titanium alloys such as super elastic or linear elastic nitinol, nickel-chromium alloy, nickel-chromium-iron alloy, cobalt alloy, or the like; or other suitable material. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

The entire shaft 14 can be made of the same material, or in some embodiments, can include portions or sections, for example portions 20 and/or 22, that are made of different materials. In some embodiments, the material used to construct shaft 14 is chosen to impart varying flexibility and stiffness characteristics to different portions of shaft 14. For example, proximal portion 20 and distal portion 22 may be formed of different materials (i.e., materials having different moduli of elasticity) resulting in a difference in flexibility. In some embodiments, the material used to construct proximal portion 20 can be relatively stiff for pushability and torqueability, and the material used to construct distal portion 22 can be relatively flexible by comparison for better lateral trackability and steerability. For example, proximal portion 20 can be formed of, for example, straightened 304v stainless steel wire, and distal portion 22 can be formed of, for example, a straightened super elastic or linear elastic alloy (e.g., nickel-titanium) wire.

Shaft 14 can have a solid cross-section as shown, but in some embodiments, can have a hollow cross-section. In yet other embodiments, shaft 14 can include a combination of areas having solid cross-sections and hollow cross sections. Shaft 14 can be continuously tapered, can have a tapered section or a number or series of tapered sections of differing diameters, or can have a constant diameter. In some embodiments, shaft 14 is tapered or otherwise formed to have a geometry that decreases in cross sectional area toward the distal end thereof. If tapered, shaft 14 can include a uniform or a non-uniform transition of the sections, depending on the transition characteristics desired. For example, shaft 14 may be linearly tapered, tapered in a curvilinear fashion, or tapered in a step-wise fashion. The angle of any such tapers can vary, depending upon the desired flexibility characteristics. The length of the taper may be selected to obtain a more (longer length) or less (shorter length) gradual transition in stiffness.

Similar to what is described above, the structure used to construct shaft 14 can be designed such that proximal portion 20 is relatively stiff for pushability and torqueability, and distal portion 22 is relatively flexible by comparison for better lateral trackability and steerability. For example, in some embodiments, proximal portion 20 has a constant or generally uniform diameter along its length to enhance stiffness. However, embodiments including a proximal portion having a tapered portion or a series of tapered portions are also contemplated. The diameter of proximal portion 20 of shaft 14 is sized appropriately for the desired stiffness characteristics dependent upon the material used. For example, in some embodiments, proximal portion 20 can have a diameter in the range of about 0.010 to about 0.025 inches or greater, and in some embodiments, in the range of about 0.010 to about 0.018 inches or greater.

Distal portion 22 can likewise be constant diameter, can be continuously tapered, or can have a tapered section or a number or a series of tapered sections of differing diameters. In embodiments where the structure of shaft 14 is designed such that distal portion 22 is relatively flexible by comparison to proximal portion 20, distal portion 22 typically does include at least one tapered or reduced diameter portion for better flexibility characteristics.

The lengths of the proximal and distal portions 20/22 are typically dictated by the length and flexibility characteristics desired in the final medical device. In some embodiments, proximal portion 20 typically has a length in the range of about 50 to about 300 centimeters, and distal portion 22 typically has a length in the range of about 3 to about 50 centimeters.

In embodiments where different portions of shaft 14 are made of different material, the different portions are connected using any suitable connecting techniques. For example, the different portions of the core wire can be connected using welding, soldering, brazing, adhesive, or the like, or combinations thereof. Additionally, some embodiments can include one or more mechanical connectors or connector assemblies to connect the different portions of the core wire that are made of different materials. The connector may comprise any structure generally suitable for connecting portions of a guidewire. One example of a suitable structure includes a structure such as a hypotube or a coiled wire which has an inside diameter sized appropriately to receive and connect to the ends of proximal portion 20 and distal portion 22. Some methods and structures that can be used to interconnect different shaft sections are disclosed in U.S. patent application Ser. No. 09/972,276, which is incorporated herein by reference.

Shaft 14 can also include an outer coating or sheath. Suitable material for use as the outer sheath include any material that would give the desired adhesion, flexibility or other desired characteristics. Some suitable materials include polymers, and like material. Examples of suitable polymer material for use as the outer sheath can include any of a broad variety of polymers generally known for use on guidewires (e.g., in guidewire core coatings or tie layers between guidewire core coatings and guidewire cores), and which have the desired characteristics. Some examples of such coatings and tie layers and materials and methods used to create such tie layers and coating can be found in U.S. Pat. Nos. 6,139,510 and 5,772,609, which are incorporated herein by reference.

Distal tip 12 can be coupled to shaft 14 using any generally suitable technique or construction. In some embodiments, distal tip 12 can be attached to distal portion 22 of shaft 14 by adhesive, welding, brazing, soldering, thermal bonding, crimping, swaging, or other suitable attachment techniques. Distal tip 12 can be preformed into the desired shape prior to connection to shaft 14, or can be formed into the desired shape during or after connection to the shaft 14. The distal tip 12 can be given the desired shape using any generally suitable technique or construction, depending upon the materials used to make the tip. In some embodiments, the tip 12 is shaped through molding, casting, grinding, thermoforming or thermal-reforming, and the like. In alternate embodiments distal tip 12 can be integral with or be a portion of shaft 14 (i.e., be a part of distal portion 22). It can be appreciated that a number of variations for generally coupling distal tip 12 and shaft 14 can be substituted without departing from the spirit of the invention.

Distal tip 12 includes an outer layer shown in FIG. 1 as outer member 16. In some embodiments, outer member 16 can comprise an outer sheath defining an inner lumen 17. In general, the outer sheath 16 is comprised of a generally flexible material. Some suitable materials for outer member 16 include polymers, metals, or metal alloys. Some examples of suitable polymers include, but are not limited to, polyethylene, polyamide, elastomeric polyamides, polyurethane, silicones, polyether-ester (for example, a polyether-ester available under the tradename HYTREL), block copolymer such as polyether block amide (PEBA) (for example that available under the trade name PEBAX®, or mixtures, combinations, or copolymers thereof. Outer member 16 may be a single polymer, multiple layers, or a blend of polymers. Some examples of suitable metals and metal alloys include stainless steel, nickel-titanium alloys (e.g., super elastic or linear elastic nitinol), nickel-chromium alloy, nickel-chromium-iron alloy, cobalt alloy, or other suitable materials.

In some embodiments, the material of distal tip 12 (and, thus, outer member 16) has a higher degree of flexibility than shaft 14. In some embodiments, the tip material includes a polymer that is more flexible than the shaft 14. In some alternative embodiments, the last portion of tip 12 at its distal end can be made of a different material from the tip material to form a tip extension. In some such embodiments, the last portion is made from a material that is more durable relative to the softer tip material. In particular, the more durable material will resist deforming or tearing when in use, such as in tracking the patient's tortuous anatomy. For example, this last portion can be manufactured from Marlex high-density polyethylene. In some embodiments, this distal tip material selection can improve the integrity of the tip region at its distal-most end.

In some embodiments, outer member 16, or portions thereof, can include, be made of, be plated with, or be doped with, a marker material to make outer member 16, or portions thereof, more visible when using certain imaging techniques, for example, fluoroscopy techniques. For example, any suitable radiopaque material known in the art can be used. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten, tungsten alloy, plastic material loaded with a radiopaque filler, for example barium subcarbonate powder, and the like, or combinations, alloys, or mixtures of any such materials and the like. In some embodiments, outer member 16 can include different sections having different amounts of loading with radiopaque material. For example, outer member 16 could include a distal section, and a proximal section, wherein the distal section has a higher level of loading with radiopaque material than the proximal section. In some embodiments, it is also contemplated that a separate radiopaque member or a series of radiopaque members, such as radiopaque coils, bands, tubes, or other such structures could be attached to or within the sleeve or other portions of device 10, or incorporated into shaft 14 by plating, drawing, forging, or ion implantation techniques.

One or more balls 18 are disposed within lumen 17 of outer member 16. The descriptive term "balls" is not intended to limit balls 18 to any particular structure, shape, or size. It can be appreciated that balls 18 could alternatively be described as beads, inner members, etc. Balls 18 can be generally metallic. For example, balls 18 may be comprised of nickel-titanium alloy, stainless steel, or any other suitable metal. Alternatively, balls 18 can be comprised of a polymer, metal-polymer composite, ceramic, glass, the like, or other suitable materials including any of those listed herein. For example, in some embodiments, balls 18, or portions thereof, can include, be made of, be plated with, or be doped with, an imaging material, such as radiopaque material, to make one or more of the balls 18, or portions thereof, more visible when using certain imaging techniques, for example, fluoroscopy techniques.

Balls 18 can have a number of different shapes and sizes. For example, balls 18 can be generally spherical. Alternatively, balls 18 can be elliptical, cylindrical, or any other suitable shape. In general, the shape and/or size of balls 18 are intended to fit within lumen 17 defined by outer member 16. For example, balls 18 can be designed so that one or more surfaces of balls 18 are in contact with the inner surface of outer member 16. According to this embodiment, balls 18 may have a diameter that is generally the same or slightly smaller than the inside diameter of lumen 17. Alternatively, balls 18 can be shaped and/or sized so as to be able to fit within outer member 16 without contacting a surface of outer member 16. According to this embodiment, balls 18 may be slightly or substantially smaller than the dimensions listed above. In some embodiments, the balls 18 can have a diameter in the range of about 0.005 to about 0.030 inches. In addition, a number of differently shaped or sized balls 18 may be used within a single distal tip 12. For example, distal tip 12 may include a number of spherical balls 18 and a number of elliptical balls 18 that may or may not vary in size. Additionally, lumen 17 can have a constant diameter or can vary in diameter. For example, lumen 17 can have a continuously tapered or stepwise variation in diameter along its length. In some embodiments lumen 17 can have an inside diameter in the range of about 0.005 to about 0.030 inches.

The number of balls 18 can vary in different embodiments. In general, one or more balls 18 may be disposed within outer member 16. In some embodiments, the number of balls 18 may generally increase as the length of distal tip 12 increases. For example, the number of balls 18 may range from 1 to about 1000 or more. Balls 18 may also vary in their relative proximity to one another. For example, balls 18 can be arranged to be "tightly packed" within lumen 17 of outer member 16 as shown in FIG. 1. Alternative embodiments can vary the level of packing and/or the number of balls within distal tip 12. Some examples of some such embodiments are shown and described below with reference to later figures.

Additionally, in some embodiments, a coating, for example a lubricious (e.g., hydrophilic) or other type of coating may be applied over portions or all of tip 12, shaft 14, outer member 16, balls 18, or other portions of device 10. Hydrophobic coatings such as fluoropolymers provide a dry lubricity which improves the handling of medical device 10 and device exchanges. Lubricious coatings improve steerability and improve lesion crossing capability. Suitable lubricious polymers are well known in the art and may include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In one example, shaft 14 is coated with a hydrophilic polymer as discussed above, and tip 12 is coated with a fluoropolymer, such as polytetrafluroethylene (PTFE).

Figure 2:
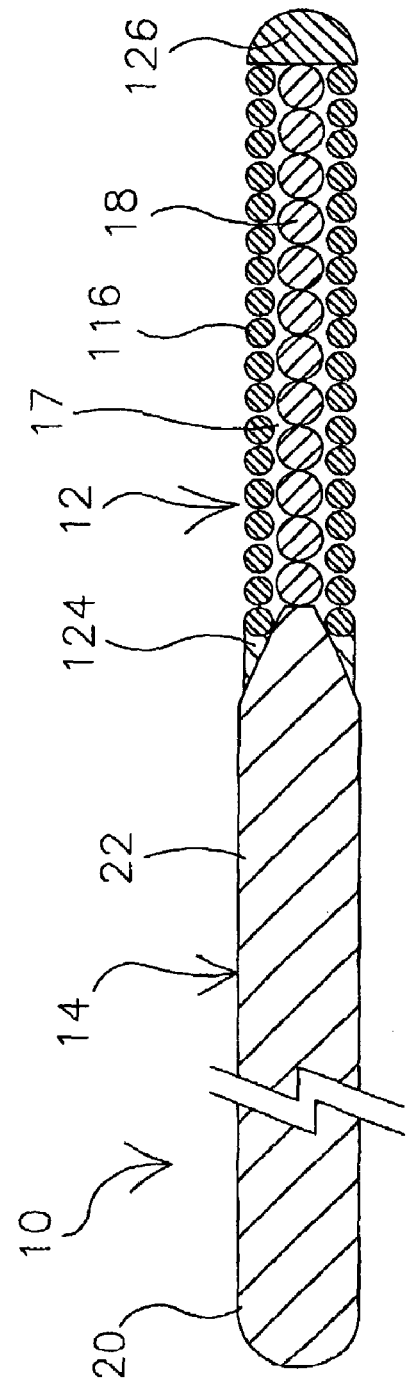
FIG. 2 is a cross-sectional view of an alternative medical device, wherein the outer member is a coil.

FIG. 2 is a cross-sectional view of an alternative embodiment of a guidewire 10, wherein outer member 116 comprises a coil. Coil 116 may be made of a metal, metal alloy, polymer, metal-polymer composite, or the like, or combinations thereof, or any other suitable material. Some examples of material for use in the coil include stainless steel, nickel-chromium alloy, nickel-chromium-iron alloy, cobalt alloy, nickel-titanium alloy, or combinations thereof, or other suitable materials. In some embodiments, the coil material can include straightened super elastic or linear elastic alloy (e.g., nickel-titanium) wire, or alternatively, a polymer material, such as a high performance polymer. In some embodiments, coil 116, or portions thereof, can be made of (in full or in part), coated with, or doped with an imaging material, such as radiopaque material, to make one or more portions of the coil 116, or portions thereof, more visible when using certain imaging techniques, for example, fluoroscopy techniques.

Coil 116 may be formed of round or flat wire or ribbon ranging in dimensions to achieve the desired flexibility and be wrapped in a helical fashion by conventional winding techniques. The coil is wound such that an inner lumen 17 is formed. The pitch of adjacent turns of coil 116 may be tightly wrapped so that each turn touches the succeeding turn or the pitch may be set such that coil 116 is wrapped in an open fashion. Moreover, the pitch of the coil 116 can be varied along the length thereof. Additionally, the thickness or diameter of the coil (and, thus, outer member 116) may be varied along the longitudinal axis of outer member 116 or among differing embodiments. For example, outer member 116 may have a thickness of about 0.0015 to about 0.0030 inches or greater at various locations along the length of outer member 116. Additionally, the coil can be formed such that the lumen 17 can have a constant diameter or can vary in diameter. For example, lumen 17 can have a continuously tapered or stepwise variation in diameter along its length. In some embodiments lumen 17 can have an inside diameter in the range of about 0.005 to about 0.030 inches.

Outer member 116 can be connected to shaft 14 using any generally suitable technique or construction. In some embodiments, outer member 116 can be attached to distal portion 22 of shaft 14 by adhesive, welding, brazing, soldering, thermal bonding, crimping, swaging, or other suitable attachment techniques. In some embodiments, a proximal weld 124 can be used, as shown in FIG. 2. In general, proximal weld 124 can be a solder weld that is designed to smooth the transition in outer diameter between shaft 14 and outer member 116. Although described as a weld, proximal weld 124 could also comprise a polymeric bridging member, heat-shrink tube, or other suitable means for joining outer member 116 and shaft 12.

A distal ball tip 126, such as a polymer or solder tip, and the like, can be disposed at the distal-most end of outer member 116. Distal ball tip 126 may be used to give medical device 10 a generally atraumatic tip so as to minimize trauma to tissue when navigating device 10 through the vasculature. A number of known methods may be used to attach distal solder ball tip 126 to outer member 116, for example, adhesive, welding, brazing, soldering, thermal bonding, crimping, swaging, or other suitable attachment techniques. Alternative methods may be substituted without departing from the spirit of the invention.

In some embodiments, outer member 116 may be coated and/or plated with another layer or material. For example, in some embodiments, outer member 116 can be coated with a protective, lubricious, hydrophilic, or other coating, or combinations thereof, such as those discussed above in the embodiment of FIG. 1. The coating can be configured to coat outer member 116 in its entirety, a portion along the longitudinal axis of tip 12, and/or a particular surface of outer member 116 (e.g., the outer surface or inner surface), and/or other portions of the guidewire 10.

Figure 3:
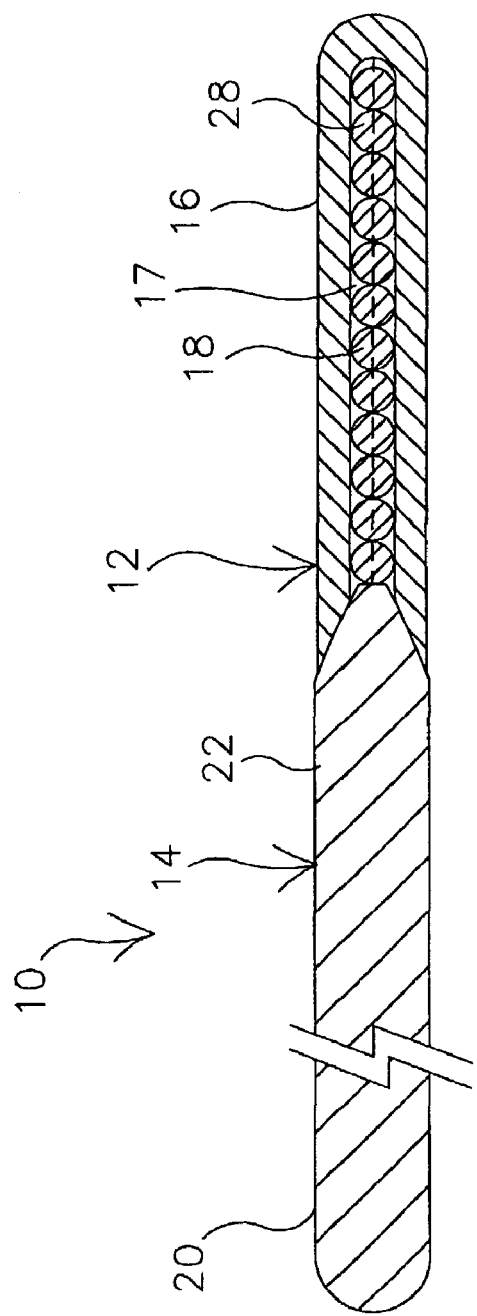
FIG. 3 is a cross-sectional view of a second alternative medical device having a structure disposed at the distal tip that extends through the balls.

FIG. 3 is a cross-sectional view of another embodiment of a guidewire 10 like that shown in FIG. 1, but further comprising an inner elongate structure 128, for example a shaft, wire, or ribbon, disposed within outer member 16. In the embodiment shown, the structure 128 is a ribbon, but other elongated structures are contemplated. In general, structure 28 can be attached to distal portion 22 of shaft 14 and extend along the longitudinal axis of distal tip 12 using suitable attachment techniques, for example, adhesive, welding, brazing, soldering, thermal bonding, crimping, swaging, or other suitable attachment techniques. In some embodiments, structure 28 may extend through shaft 14 in the proximal direction to provide additional structural support. Additionally, in some embodiments, the structure 28 can be attached to the distal portion of the outer member 16 using suitable attachment techniques.

Within outer member 16, structure 28 may pass or extend through balls 18. In order to facilitate this feature, balls 18 may include a lumen or channel for structure 128 to pass through. In some embodiments, the channels within balls 18 may be sized for a "snug" or friction fit with structure 28, or can be otherwise attached to the structure 28 using suitable attachment techniques, such as adhesive, welding, brazing, soldering, thermal bonding, crimping, swaging, and the like. According to this embodiments the longitudinal position of balls 18 along structure 28 is substantially fixed. Alternatively, the channels within balls 18 may be sized to allow free movement of balls 18 along structure 28. Fixing or allowing free movement of balls within the distal tip 12 can provide for varying degrees of flexibility along the length of distal tip 12. Such features may enhance the ability of medical device 10 to navigate the vasculature by allowing device 10 to adapted to different flexibility demands.

Structure 28 may generally be made of or include any suitable material, for example metals, metal alloys, polymers, combinations thereof and the like. Some examples of suitable metals and metal alloys include stainless steel, nickel-chromium alloy, nickel-chromium-iron alloy, cobalt alloy, nickel-titanium alloy, or combinations thereof, or other suitable materials. In some embodiments, the structure 28 material can include straightened super elastic or linear elastic alloy (e.g., nickel-titanium) wire, or alternatively, a polymer material, such as a high performance polymer. In some embodiments, structure 28, or portions thereof, can be made of (in full or in part), coated with, or doped with an imaging material, such as radiopaque material, to make one or more portions of the structure 28, or portions thereof, more visible when using certain imaging techniques, for example, fluoroscopy techniques.

The thickness of structure 28 may also be varied. For example, structure 28 may have a thickness of about 0.005 to about 0.030 inches or more. Moreover, the thickness of structure 28 may be varied along its length. For example, a proximal portion of structure 28 may be thicker than a distal portion.

Figure 4:
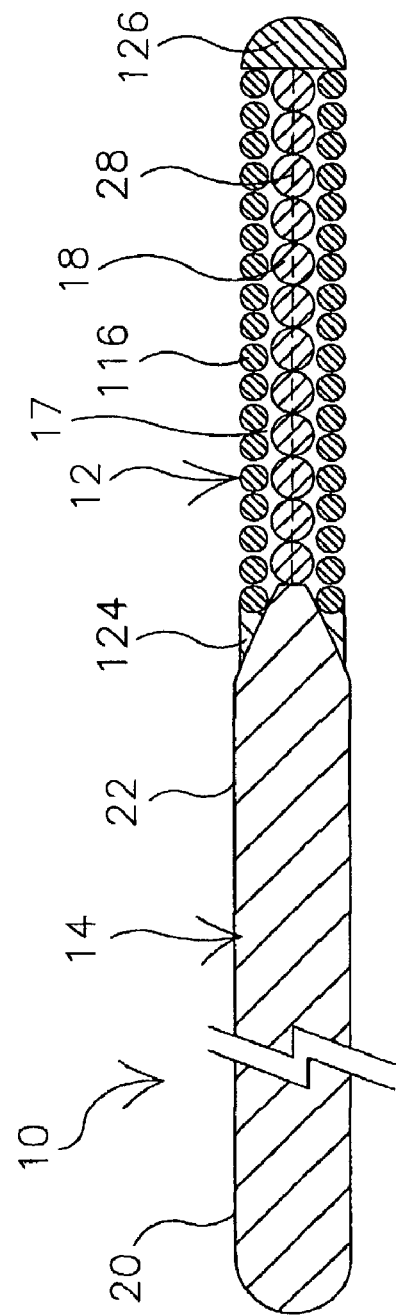
FIG. 4 is a cross-sectional view of a third alternative medical device including a structure extending through the balls and wherein the outer member is a coil.

FIG. 4 is a cross-sectional view of another alternative embodiment of a medical device 10 similar to that described in FIG. 2, and includes most of the structural features described above if FIG. 2. However, the embodiment of FIG. 4 includes a structure 28 as in FIG. 3. Similar to what is described in reference to FIG. 3 above, structure 28 may be attached or extend through shaft 14. The distal end of structure 28 is attached to distal solder ball tip 126. The distal end of structure 28 may be attached or joined to distal solder ball tip 126 by any suitable means, for example through adhesive, welding, brazing, soldering, thermal bonding, crimping, swaging, or other suitable attachment techniques.

FIG. 5 is a cross-sectional view of another embodiment of a medical device 10 similar to that in FIG. 1, but wherein balls 18 are loosely associated within lumen 17 of outer member 16. By loosely associating or allowing space to be present between balls 18, the flexibility of distal tip 12 can be altered. For example, increasing the space between balls 18 can generally increase the flexibility of distal tip 12. It can be appreciated that the spacing between balls 18 can be altered by a number of different methods. For example, by disposing fewer balls 18 within lumen 17, balls 18 have a greater area to move within lumen 17 and create spaces there between. Alternatively, spacing between balls 18 may be accomplished by using differently sized or shaped balls 18. For example, a number of generally small balls 18 (e.g., small enough to be freely movable within outer member 16) may be separated by a number of generally larger balls 18 (e.g., large enough to generally contact a substantial portion of the inner surface of outer member 16 and, thus, be substantially immobile). This embodiment may be further modified by altering the numbers of balls 18 or similarly accomplished using different shaped balls 18.

As alluded to above, alterations in the configuration and/or spacing of balls 18 within lumen 17 of outer member 16 may be incorporated within any of the embodiments contemplated above. For example, the configuration of balls 18 may be altered in combination with structure 28.

Similarly, FIG. 6 is a cross-sectional view of another embodiment of a medical device 10 similar to that in FIG. 2, but wherein balls 18 are loosely associated in combination with outer member 116 wherein outer member 116 is a coil.

From the above discussion, it should be clear that the features of medical device 10 can be incorporated into a number of different medical devices. For example, guide catheters are typically designed to have generally flexible distal ends to allow navigation through the anatomy of a patient. Other devices such as therapeutic or diagnostic catheters, endoscopic or laproscopic devices, and the like are also contemplated to be within the scope of the invention.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device, comprising:
   an elongate member having a proximal portion with a substantially solid cross-section and a distal tip portion;
   wherein the distal tip portion includes an outer member, wherein the outer member comprises a polymeric sheath that has a proximal end that remains outside a vasculature of a patient and has a distal end that is insertable into, navigable through, and removable from the vasculature of the patient; and
   one or more balls non-removably disposed within the outer member;
   wherein the balls are disposed within a lumen defined by the outer member and wherein the balls are tightly packed within the outer member such that outer surfaces of adjacent balls are in direct contact with each other;
   wherein the one or more balls are free of direct attachment to any other structure of the medical device.

2. The medical device in accordance with claim 1, wherein at least one or more of the balls comprise metal or metal alloy.

3. The medical device in accordance with claim 1, wherein at least one or more of the balls comprise polymer, glass, or ceramic.

4. The medical device in accordance with claim 1, wherein the balls are spherical.

5. The medical device in accordance with claim 1, wherein the balls are non-spherical.

6. A medical device, comprising:
   an elongate member having a proximal portion and a distal tip portion;
   wherein the distal tip portion includes an outer member;
   one or more balls non-removably disposed within the outer member and tightly packed within the outer member such that outer surfaces of adjacent balls are in direct contact with each other, wherein the one or more balls are free of direct attachment to any other structure of the medical device; and
   wherein the outer member comprises a coil.

7. The medical device in accordance with claim 6, further comprising a distal solder tip disposed at a distal end of the outer member.

8. The medical device in accordance with claim 6, further comprising a proximal weld disposed at a proximal end of the outer member to attach the outer member to the elongate member.

9. A medical device, comprising:
   an elongate shaft having a proximal end with a substantially solid cross-section and a distal end; and
   a distal tip disposed near the distal end, the distal tip including an enclosure having one or more beads non-removably disposed therein, wherein the enclosure comprises a polymeric sheath that has a proximal end that remains outside a vasculature of a patient and has a distal end that is insertable into, navigable through, and removable from the vasculature of the patient, and wherein the beads are tightly packed within the enclosure relative to each other such that outer surfaces of adjacent beads are in direct contact with each other and the enclosure is substantially filled with beads;
   wherein the one or more beads are free of direct attachment to any other structure of the medical device.

10. The medical device in accordance with claim 9, wherein the beads comprise metal or metal alloy.

11. The medical device in accordance with claim 9, wherein the beads comprise polymer, ceramic, or glass.

12. The medical device in accordance with claim 9, wherein the beads are spherical.

13. The medical device in accordance with claim 9, wherein the beads are non-spherical.

14. A medical device, comprising:
   an elongate shaft having a proximal end and a distal end;
   a distal tip disposed near the distal end, the distal tip including an enclosure having one or more beads non-removably disposed therein, the one or more beads being tightly packed within the enclosure relative to each other such that outer surfaces of adjacent beads are in direct contact with each other and the enclosure is substantially filled with beads, wherein the one or more beads are free of direct attachment to any other structure of the medical device; and
   wherein the enclosure comprises a coil.

15. The medical device in accordance with claim 14, further comprising a distal solder tip disposed at a distal end of the enclosure.

16. The medical device in accordance with claim 14, further comprising a proximal weld disposed at a proximal end of the enclosure to attach the enclosure to the elongate shaft.

* * * * *

UNITED STATES PATENT AND TRADEMARK OFFICE
CERTIFICATE OF CORRECTION

PATENT NO.       : 7,993,285 B2                                                  Page 1 of 1
APPLICATION NO.  : 10/288173
DATED            : August 9, 2011
INVENTOR(S)      : Alan D. Eskuri It is certified that error appears in the above-identified patent and that said Letters Patent is hereby corrected as shown below:

Column 7
Line 53, delete "embodiments", and insert therefor -- embodiment, --.

Signed and Sealed this
Eleventh Day of October, 2011

David J. Kappos
*Director of the United States Patent and Trademark Office*